United States Patent [19]
Massie et al.

[11] Patent Number: 5,822,036
[45] Date of Patent: Oct. 13, 1998

[54] EYE IMAGING UNIT HAVING A CIRCULAR LIGHT GUIDE

[75] Inventors: Norbert A. Massie, San Ramon; Wei Su, Livermore, both of Calif.

[73] Assignee: Research Development Foundation, Carson City, Nev.

[21] Appl. No.: 820,224

[22] Filed: Mar. 18, 1997

Related U.S. Application Data

[63] Continuation-in-part of Ser. No. 685,725, Jul. 24, 1996.

[51] Int. Cl.$^6$ ...................................................... A61B 3/00
[52] U.S. Cl. ............................................ 351/219; 351/221
[58] Field of Search ...................................... 351/205, 206, 351/212, 247, 219, 221

[56] References Cited

U.S. PATENT DOCUMENTS

| | | | |
|---|---|---|---|
| 3,630,602 | 12/1971 | Herbert | 351/16 |
| 3,944,341 | 3/1976 | Pomerantzeff | 351/7 |
| 3,954,329 | 5/1976 | Pomerantzeff | 351/16 |
| 4,023,189 | 5/1977 | Govignon | 354/62 |
| 4,026,638 | 5/1977 | Govignon | 351/221 |
| 4,200,362 | 4/1980 | Pomerantzeff | 351/16 |
| 4,573,778 | 3/1986 | Shapiro | 351/219 |
| 4,715,703 | 12/1987 | Cornsweet et al. | 351/205 |
| 5,125,730 | 6/1992 | Taylor et al. | 351/206 |

FOREIGN PATENT DOCUMENTS 4232280  3/1994  Germany ............................. 351/221

Primary Examiner—Huy Mai
Attorney, Agent, or Firm—Fulbright & Jaworski

[57] ABSTRACT

An eye imaging system having a portable image capture unit having a circular light guide positioned adjacent to and behind a corneal contact lens for controlling directing light over a wide field to the retina of an eye and provide more light towards the center of the eye.

16 Claims, 12 Drawing Sheets

FIG. IC

EYE IMAGING UNIT HAVING A CIRCULAR LIGHT GUIDE

RELATED APPLICATION

This application is a continuation in part of copending application Ser. No. 08/685,725, filed Jul. 24, 1996, entitled PORTABLE IMAGING CAPTURE UNIT FOR THE EYE.

BACKGROUND OF THE INVENTION

Cameras for imaging the eye must meet several technical objectives. It is preferable, and for some clinical diagnoses required, to obtain color images of the eye. Also, in some instances, near infrared images are required. For some applications, an eye imaging camera should offer the option of providing very high spatial resolution for diagnosis of certain ocular diseases. For example, when examining the neural fiber layer, high resolution is required.

Moreover, wide field-of-view (FOV) images of the eye are necessary for evaluating some pathologies and a prime example of this is ocular tumors which lie in many cases on the periphery of the retina. When examining only the optical disk, a 30 degree wide FOV is sufficient. For studies of tumors located on the periphery of the retina and other retinal disorders, a FOV of 120 degrees and even larger is preferred.

The intensity of light required for imaging is also a consideration as the level required to expose many films can be very uncomfortable to the patient. Scattering and reflection of the illumination light from surfaces other than the retina can substantially reduce the contrast of the image. Imaging using electronic array sensors such as charged coupled devices (CCD) instead of film is highly desired as well. Electronic array cameras tend to be more sensitive than film, reducing the amount of light required. Also, electronic sensors and displays allow instant review of the image and various image processing opportunities are immediately available and immediate transmission of electronic images to remote locations is possible.

While there are retinal cameras which provide some of the above features to various degrees, there is currently no commercially available camera meeting the requirement for wide FOV digital CCD imaging. Problems especially associated with wide FOV imaging are the uniformity of illumination, scattering of the illumination back into the camera from locations other than the retina, the resolution and distortion of the image, the cost and difficulty of manufacture of the optical system, and obtaining a sufficient FOV.

The refraction of the light as it exits the eye into air leads to significant problems for the wide FOV camera. Light coming from the periphery of the retina strikes the corneal-air interface at oblique angles. These rays can be bent sufficiently so that they do not exit the cornea. This leads to a phenomenon known as total internal reflection (TIR). To avoid TIR, it is necessary to provide a contact lens against the cornea as a part of the optical system. An appropriate refractive index for the contact lens can be selected which will defeat TIR.

Though certain problems are eliminated with the contact lens feature, there still remains the perplexing issue of wide field illumination and a workable solution to this problem is a feature of this application. In U.S. Pat. No. 3,954,329, O. Pomerantzeff teaches the use of illumination through the sclera. However, the color of the light is affected by transmission through the sclera and the amount of light reaching the retina is reduced. In U.S. Pat. No. 3,630,602, J. Herbert teaches the use of "cold" light (light with the infrared wavelengths filtered out) and illumination in the area surrounding the contact lens. This system however suffers from significant backscattering. In U.S. Pat. No. 3,944,341 Pomerantzeff teaches the use of two rings of fiber optics surrounding the contact lens. However, as we shall discuss at length, this concept suffers from significant performance and manufacturing limitations and has failed to pass the test of merchantability.

Optimally, input light travels in paths to the retina such that back reflections from portions of the eye lens do not travel the same path as the reflections from the retina. Back reflections are well known to degrade the contrast of the image. In U.S. Pat. No. 3,944,341, multiple ring style fiber optic illuminators are shown. In the '341 patent, light is injected by a fiber optic ring around the periphery of the contact lens. The fiber is held in place by being potted and then the entire structure is ground and polished to the same radius as the contact lens. Thus, the periphery of contact lens and the radius at which the fiber is placed sets the direction of the central ray of the fiber illumination and the divergence of the light is set by the fiber design. One faces the problem of injecting light from this ring in a manner such that light is not occluded by the iris and uniformly illuminates the retina at wide FOV. The constraint on the location and angle of the injected light in this design and the divergence as set by the fiber design rather than being optimized for the illumination system provides significant performance limitations. Note that optical fibers tend to have far-field profiles which are Gaussian and thus the illumination profile at the retina is not uniform. Again, these are sources by lack of freedom of the direction and divergence of the illumination and, in fact, is unsatisfactory for the objectives of the wide FOV camera.

It is thus recognized that a simple single ring may not be satisfactory for illumination of a wide field of the retina and in U.S. Pat. No. 3,944,341, the use of two rings of fibers is proposed. One ring illuminates the interior angles of the retina, while the other illuminates the exterior angles. Yet, even with this design, one is forced to allow the lens diameter to dictate the central ray angle of illumination and, thus, the area illuminated and the limitations of Gaussian non-uniformity's of illumination still represent a problem.

In U.S. Pat. No. 4,023,189 J. Govignon teaches the placement of a pupil at the eye to reduce glare but offers no additional solution to the wide field illumination problem.

Even though the two ring approach seems to offer wider FOV illumination, it faces other significant challenges including expense in manufacture as well as non-uniformity of the illumination. The fibers and the contact lens must be held in place and potted (note that the entire assembly is quite small and very difficult to handle.) Then, the entire structure, including the fiber pigtail, must be transported to an optical shop and ground and polished. While this is possible, it is difficult in practice, and is a serious economic barrier. Further, for most potting compounds, the refractive index is such that light will leak out into the potting compound instead of being injected or focused only into the eye. Remember that fiber optics confine light due to the appropriate selection of cladding material with the assumption that they will be surrounded by air or other carefully selected material. Additionally, the potting compound must be compatible with sterilization procedures and it must be non-porous to assure that pathogens are not harbored in the device and transmitted between patients. All these elements together make the manufacturing and use of fiber optic composite rings difficult and expensive. Clearly, it would be preferable to eliminate this costly process. In conclusion, it would be of great advantage to circumvent the above limitations of both performance and manufacture derived from the prior art fiber ring approach.

Instead of the complex, limited, and expensive dual fiber optic rings it would be of great advantage to use a machined or ground and polished one piece plastic or glass light guide ring. However, just replacement of the fiber with a plastic ring does not eliminate the key problems. To completely solve the problems it is necessary in conjunction to place this light guide behind a special front contact lens, used primarily as a transparent physical barrier. It would be further of great advantage to be able to inject the light from the ring at an arbitrarily selected angle and degree of divergence and illumination pattern. It would be of yet further advantage to avoid the potting operations and to avoid optical finishing of the final assembled nose piece.

To understand the solution to this problem we note in FIGS. 1A and 1B drawings of the eye E with a contact lens L in place with a prior art light ring of fibers F. Achieving the wide FOV imaging and illumination presents significant dilemmas to the designer which can be seen from these drawings. Note that cornea is about 10 mm in diameter and the pupil of the eye, the iris, can, even when dilated, may be no more than 4 mm.

The entrance pupil of the optical system (as relayed) is set at the eye lens to minimize aberrations and optimize rejection of scattered light; see FIG. 1A The minimum diameter and the slope of the edge of the contact lens are then set by the entrance pupil and the distance to the cornea and the FOV, as shown in FIG. 1A. For a camera with 120 degrees FOV and a 1 mm diameter entrance pupil, the minimum 6 mm diameter and the slope of the edge is 45 degree. Thus, the fiber ring F must set at a radius slightly larger, for example, 7 mm, and, in this design, its angle of injection is set to 45 degree by the slope of the contact lens L at this radius.

As shown in FIG. 1B, there is a significant problem with obtaining illumination at the center of the eye E with a single fiber ring F located at the periphery of the contact lens L. It is the result of large angle of injection and small divergence angle of optical fibers. It is also shown that a portion of light is blocked by the tissue at the periphery of the eye lens, which in turn determines the size of the illuminated area. The divergence angle of light injected from an optical fiber is limited by its numerical aperture. When in contact with the tear fluid, the divergence angle of the optical fibers is less than 40 degrees typically. This problem is not resolved by adding second ring of fibers at larger diameter, although multiple rings will allow a larger peripheral area of illumination; this is the finding of modern optical design code and are in contradiction to the claims of U.S. Pat. No. 3,944,341 and for measurements on real eyes. As shown in FIG. 1C, the light from a larger diameter ring of fibers F1 can be blocked by the eye iris. It is assumed a ring diameter of 8 mm and a eye iris diameter of 5.5 mm. As the result, the second large ring of fibers F1 only help illuminating the periphery area of the retina, but not the center area. Clearly, one needs to be able to arbitrarily set the illumination pointing direction and divergence and not have it controlled by the lens diameter and the materials of the optical fiber.

In particular, difficulty has been encountered in directing enough light onto the center of the retina. Therefore, additional consideration is required to provide improvements for directing more light towards the center of the eye.

Thus, the designer of a contact wide FOV camera faces a serious dilemma. For wide FOV and optimal placement of the entrance pupil the illumination ring is forced to be at a larger radius and at this radius the human iris can occlude the portions of the illumination needed for the center of the retina. A dark spot can be seen if the patient's iris is not dilated large enough.

SUMMARY

The object of the present invention is to provide a small, light weight, hand-held image capture unit (ICU). The ICU of the present invention contacts the retina, re-images the pupil, provides for wide field-of-view with minimal field curvature and minimized aberrations, and provides chromatic imaging with high fidelity. The advent of miniature three chip charged couple device (CCD) cameras which can be contained within the ICU increases the resolution of the image.

Thus, a specific objective of the present invention is to provide a wide field imaging unit that obtains high quality color images over 120 degrees and larger and this with highly uniform intensity of image, with low backscatter and a low-cost manufacturable design. It is also an objective to reduce the required minimum diameter of the dilated eye iris being 5.5 mm, a figure commonly found among children. Further, it is an objective to provide an imaging unit that is light weight and can be hand-held. In another embodiment, the imaging unit allows for easy insertion and removal of various light filters for angiography and allows for easy insertion and removal of lenses.

It is a particular objective of the present invention to remove the economic and technical barriers to the use of wide field contact cameras arising from the use of a fiber optic light guide. The present invention instead is directed to a portable image capture unit that provides for a one piece ring light guide made from machined plastic or ground and polished glass. The light guide is angled so that there is minimal back reflection from the eye lens to lessen the contrast of the image. A larger contact lens is used to lie between the imaging and illuminating optics to protect the cornea and this allows a vast improvement in the system performance as well as its manufacturability.

Another feature of the present invention is to provide various improvements directing more light from the light guide onto the center of the retina of the eye.

Other and further objects, features and advantages will be apparent from the following description of the presently preferred embodiments of the invention, given for the purpose of disclosure, and taken in conjunction with the accompanying drawings.

BRIEF DESCRIPTION OF THE DRAWINGS

FIG. 1C is a side, cross-sectional view of an optical system at an eye showing the illumination limitations of multiple rings of fibers in the previous art.

FIG. 5B is a top view of a pupil mask to block backscatter from the eye lens from the central illumination as shown in FIG. 5a.

DETAILED DESCRIPTION OF THE PREFERRED EMBODIMENT

As discussed above, the prior art optical systems have major deficiencies and limitations.

Figure 1A:
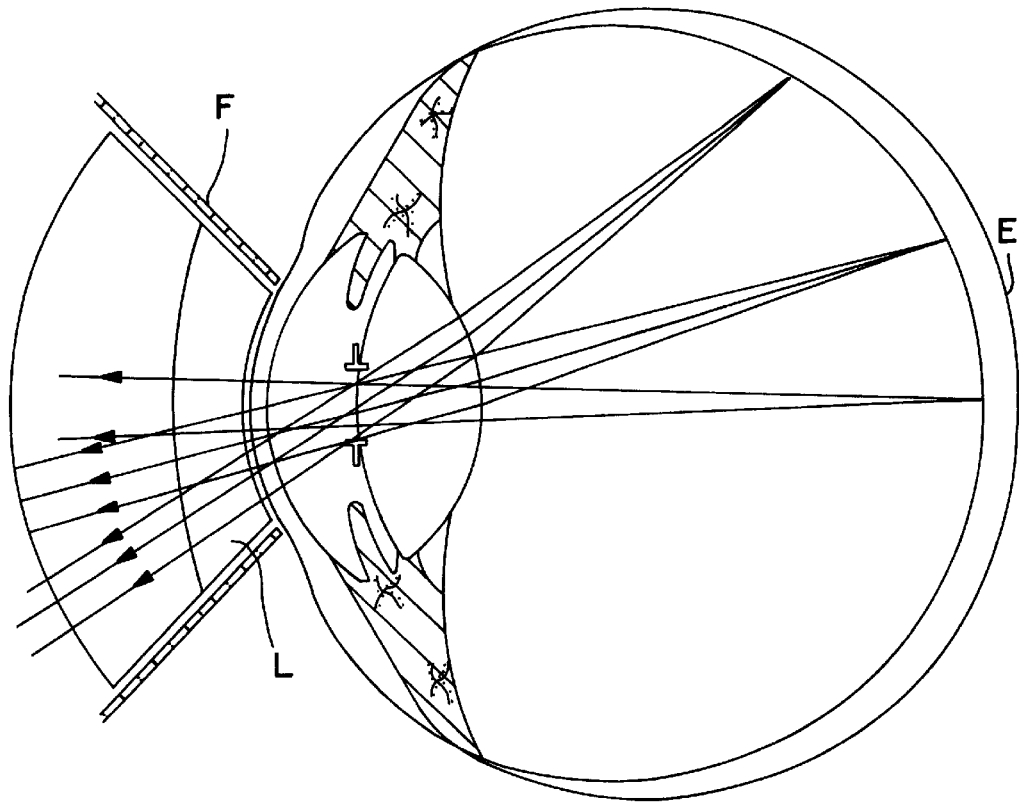
FIG. 1A is a side, cross-sectional view of an optical system at an eye showing the location of the preferred relayed entrance pupil.
Figure 1B:
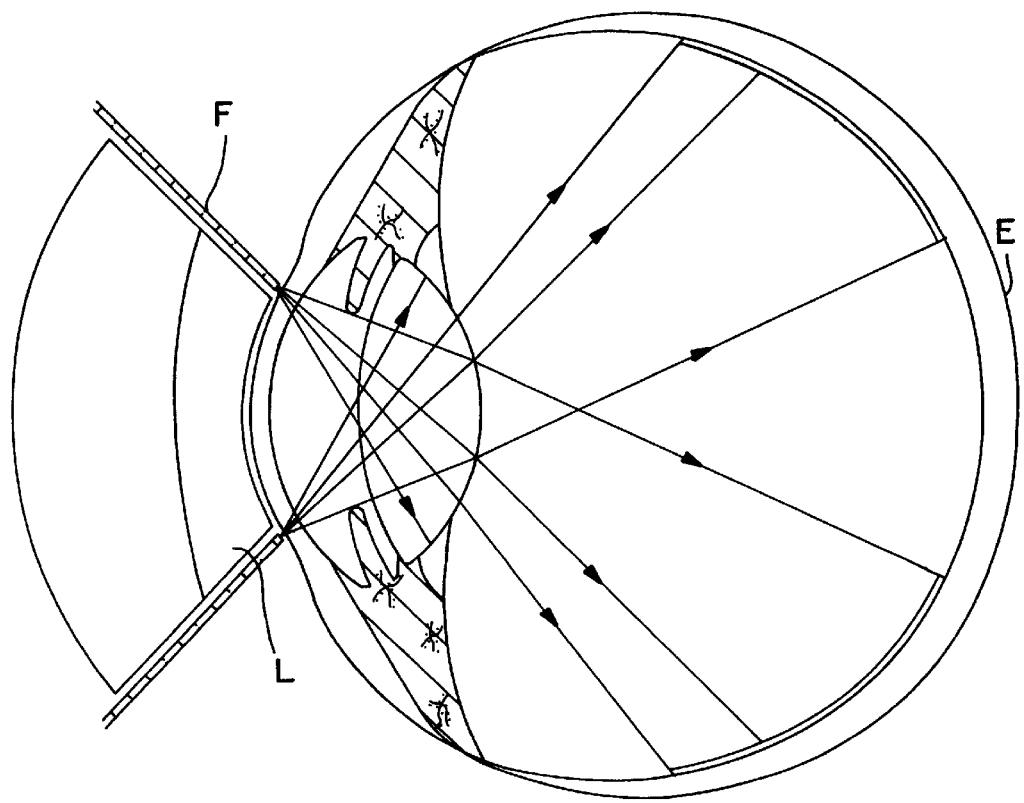
FIG. 1B is a side, cross-sectional view of an optical system at the eye showing the illumination limitations of the previous art.
Figure 2A:
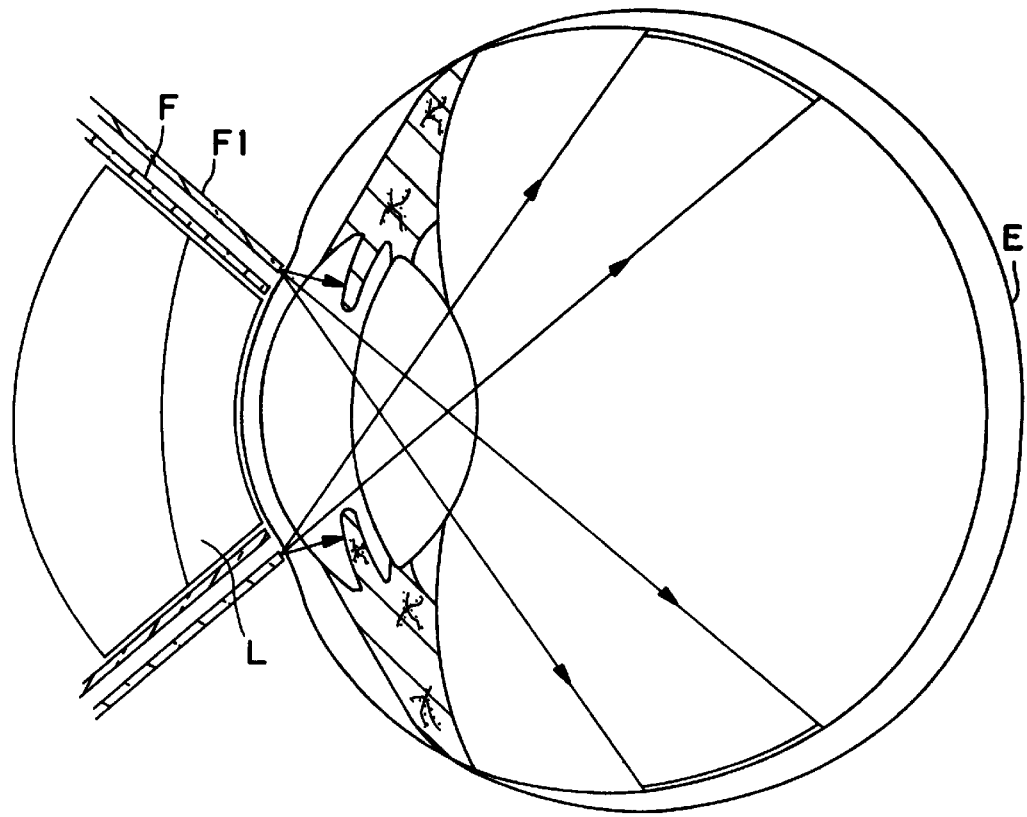
FIG. 2A shows a cross-sectional view of a light guide in place of fibers of the prior art showing that either the tears and/or potting compound would interfere with the proper operation of the light guide.
Figure 2A:
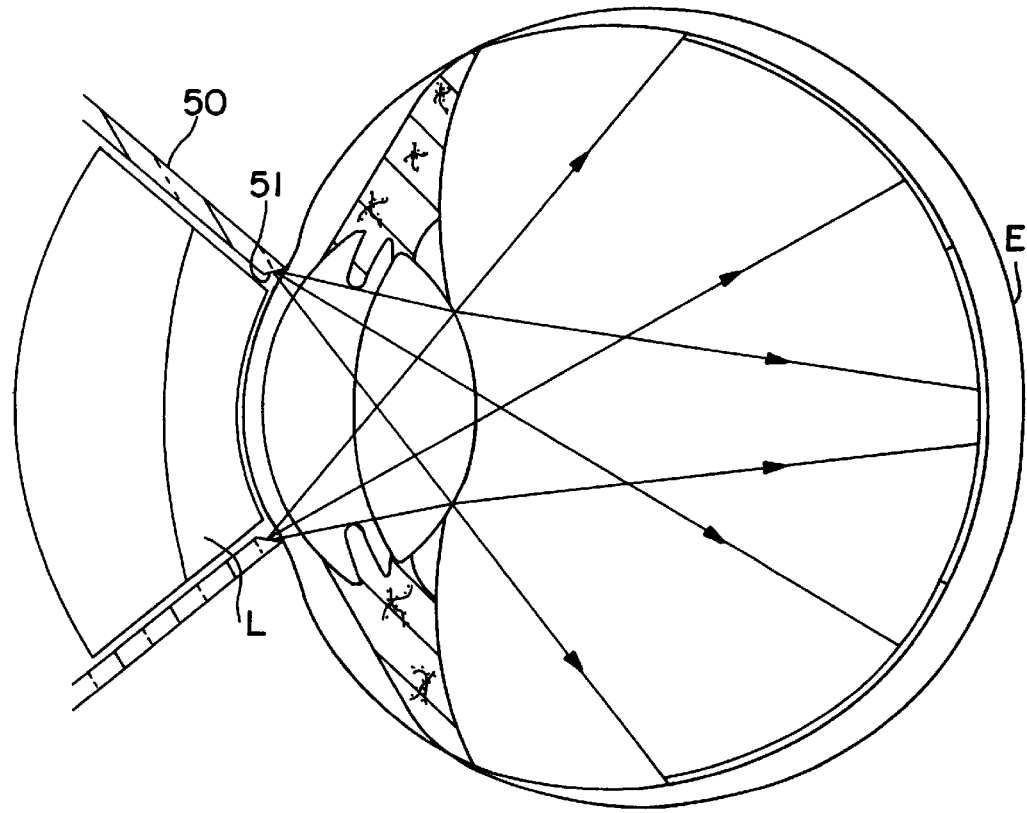
Figure 2B:
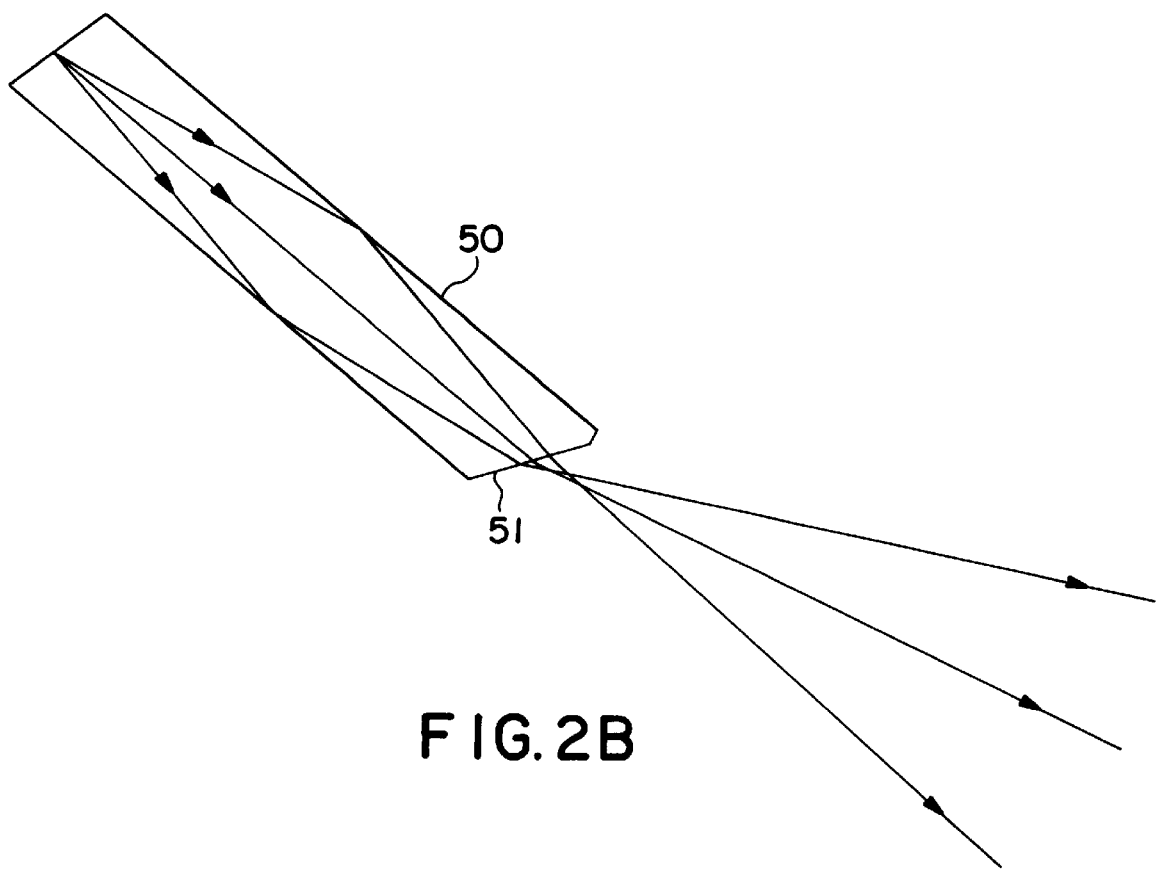
FIG. 2B is an enlarged fragmentary cross-sectional view of a light guide showing the transmission of light through the end.

As a starting point and as part of this innovation, a light guide is fabricated from a transmissive material such as plastic or glass. Any satisfactory plastic may be used such as acrylic or polycarbonate and any satisfactory glass may be used such as an optical material with high transmittance (spectrum from 450 nm to 700 nm). If the light guide is surrounded by air, the divergence angle of light injected from the light guide is controllable and can be as wide as 180 degrees. A conceptional light delivery device, shown in FIG. 2A, is designed to concentrate the light from a larger diameter tube of light guide 50 to a small ring of light guide surrounding the front lens. As shown in FIG. 2B, the end of the light guide can be shaped and the light be bent to aim in a more optimal direction. However, this innovation alone leaves major problems. First, the sharp end 57 of the guide 50 is unacceptable when touching the cornea. Second, the cavities around the end of the guide 50 will be places where germs can lodge and cross-contamination between patients would be inevitable. Third, the tear film will fill in this volume and since the tear film has an index of refraction close to most waveguide materials, the ray bending at the end of the guide which occurs when the guide is surrounded by air (index nearly equal to 1) would be nearly eliminated (tear film index is close to 1.34) As the result, the dark spot will reappear in the center of image. Fourth, the diameter of eye iris has to be dilated to be larger than 6.5 mm to prevent the blocking with a fiber ring of 6 mm diameter.

Figure 3:
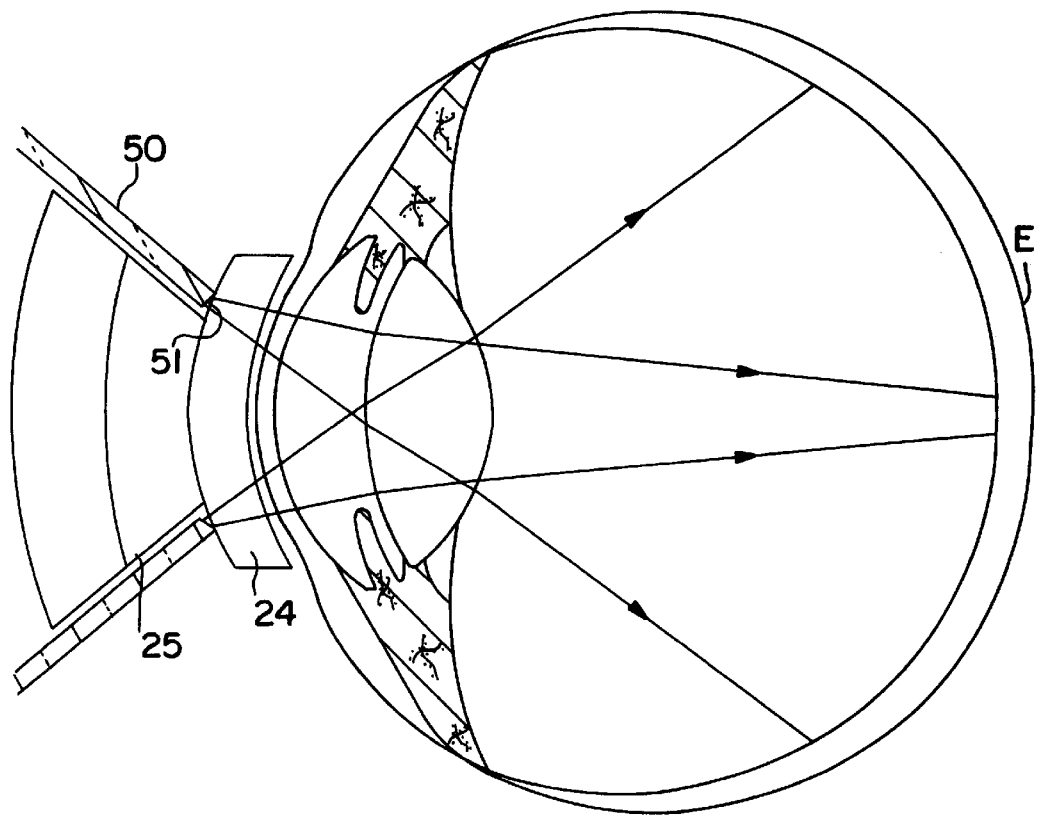
FIG. 3 shows a side, cross-sectional view of a corneal contact lens and doublet lens of the front lens group of the front lens set and the light guide of one embodiment of the present invention.

To complete this concept with a workable and manufacturable implementation, we place the entire guide 50 behind a contact or cornea glass lens 24 whose diameter is larger than the lens 25 which accumulates the return light, as shown in FIG. 3. The entrance pupil of the optical system is also moved slightly toward the contact lens to reduce the diameter of the lens to 5 mm, which in turn reduces the light guide diameter to 6 mm. In the present design, when the eye pupil is dilated to be larger than 5 mm, a 120 degree FOV can be illuminated without a dark spot in the central portions of the image. The light rays from the opposite side of light guide will be overlapped near the center of the retina, which provides more reliable illumination for this area. The light intensity distribution on the retina is also designed so that the intensity increases gradually from the center to the periphery, which will result in a more uniform intensity distribution for the image of retina. Now, only the boundary of the "contact" glass will be bonded to the case protecting the volume behind the contact lens from any incursion of eye fluids or bonding agents.

While a guide 50 with a partial cut to change the injection angle and its spread has been shown, it could just as well for example have a small lens shape on the tip 51. The contact lens 24 need not have any optical power, but it may if desired. The only bonding compound necessary will bond the edge of the contact lens 24 to the case 11 of the hand-piece 10.

The difference of index refraction between the contact glass 24 material and tear fluid, even through is small, can still cause partial reflection of light from the front surface of contact glass. Although the light guide and the imaging system are carefully designed so that the reflected light can not reach the CCD camera directly, it can still cause strong stray light which can degrade the image quality when a dark object like retina is imaged. To improve the performance, a hard, durable conventional optical antireflection coating may be added to the front surface of contact glass. Other measures, which include selectively adding absorption layer to portion of light guide surface, installing a light stop in the imaging system, can be taken to reduce the stray light. Also, the contact lens may have additional shape including a hole through which the front doublet can be mounted. The edge of the doublet is blacked so that the light traveling in the contact lens from the light guide can not enter the front doublet.

Figure 4:
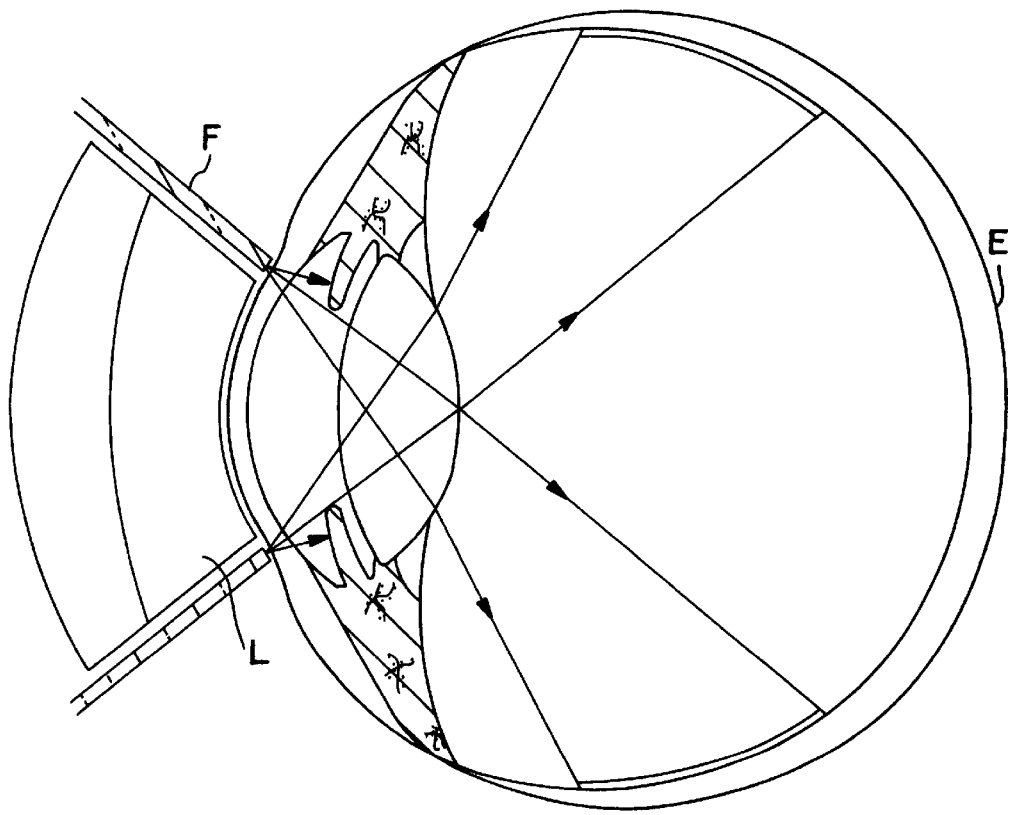
FIG. 4 is a cross-sectional view showing how a very wide FOV system using prior art fibers would only illuminate the periphery of the retina.

While the above design provides for improved performance there is still a limitation for extremely wide FOV imaging. Consider the situation shown in FIG. 4 where a very wide FOV is provided, forcing the front imaging lens to become wider. In this situation, it is not possible to illuminate the center of the retina and the periphery, regardless of how many light rings or aiming directions are used because of the blocking by the iris.

Figure 5A:
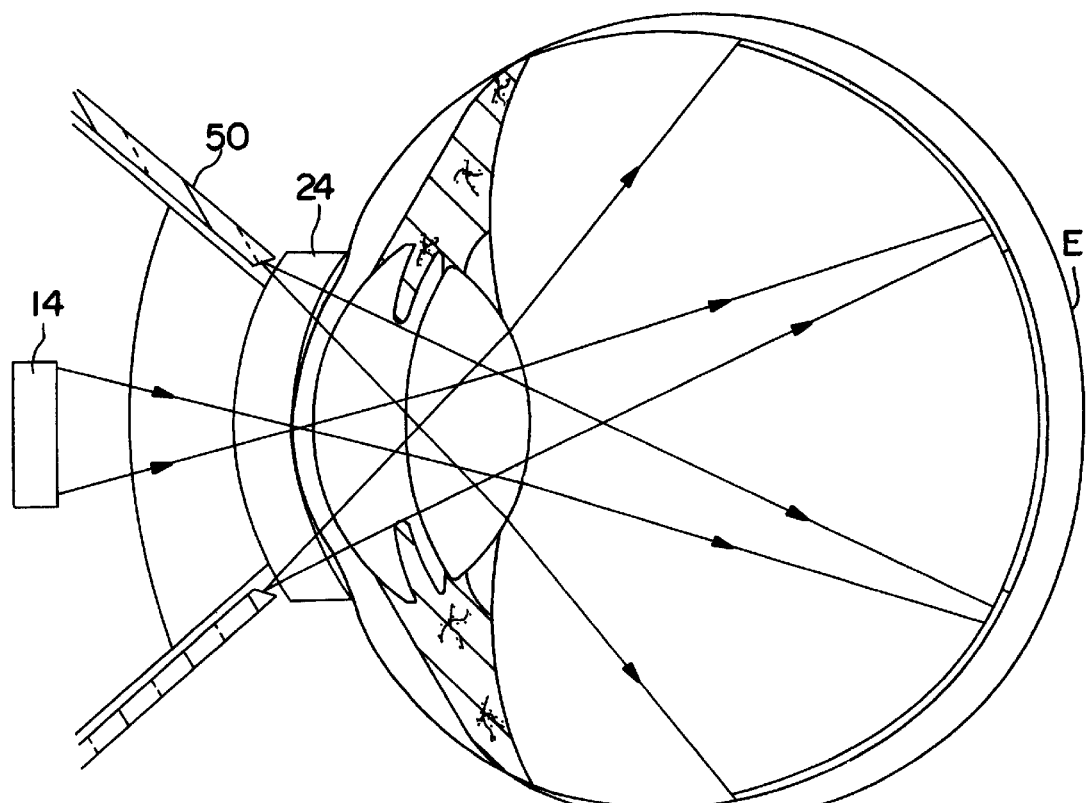
FIG. 5A is a side cross-sectional view of an optical system of the present invention with both central and circumferal illumination.
Figure 5B:
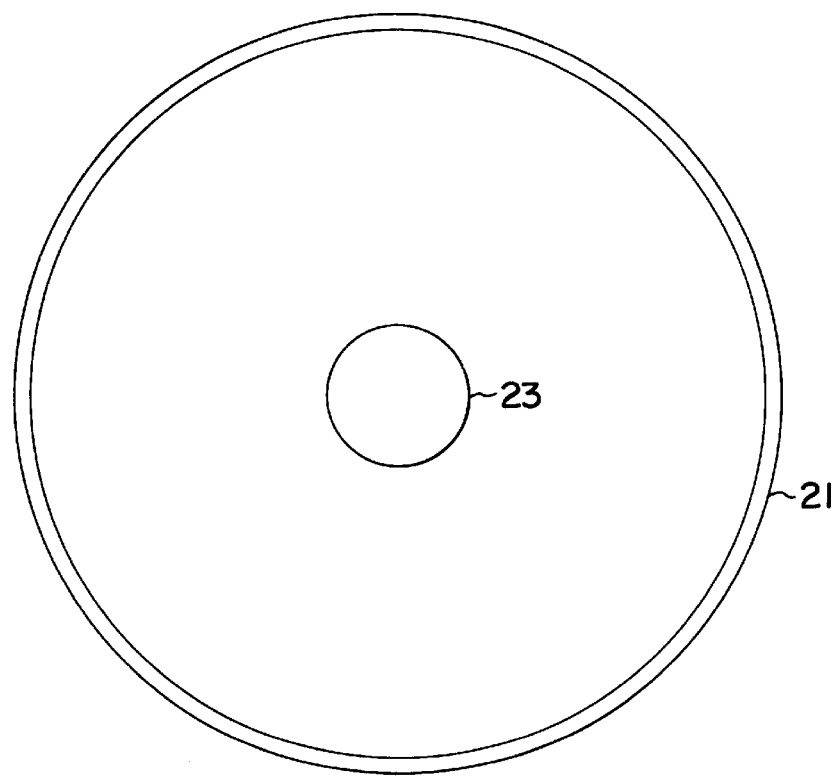

These illumination system problems can be circumvented by the design of FIG. 5A. Here, either a central optical guide is used or a beam of light from a light source 14 is projected to the imaging optical system to illuminate the central part of retina and the standard light guide is used to illuminate the periphery. Now one must contend with the backscatter from the centrally located optical feed. This can be accommodated as shown in FIG. 5B by using a pupil mask 21 with a central obstruction 23 which is positioned in (FIG. 7).

Other and further embodiments of the present invention may be provided wherein like parts are similarly numbered to those shown in FIGS. 3 and 5 with the addition of the suffixes "1" and "2". In some applications in the embodiments of FIG. 3, difficulty was encountered in directing enough light onto the center of the retina of the eye E. In this embodiment, the guide 50 has an end 51 with an angular cut which serves the function of directing the light through the contact lens 24 and towards the center of the eye E. However, at the steep angles of the end 51 which are necessary to provide the direction the reflection of the plastic light guide 50 is high and a reduced amount of light exits from the end 51. (Note that the reflectivity of all dielectrics increases with the angle of incidence.) Also in the embodiment of FIG. 3, the cornea contact glass lens 24, as shown, has essentially no power as the lens 24 is shown with the same radius of curvature on the front and on the back.

Figure 6:
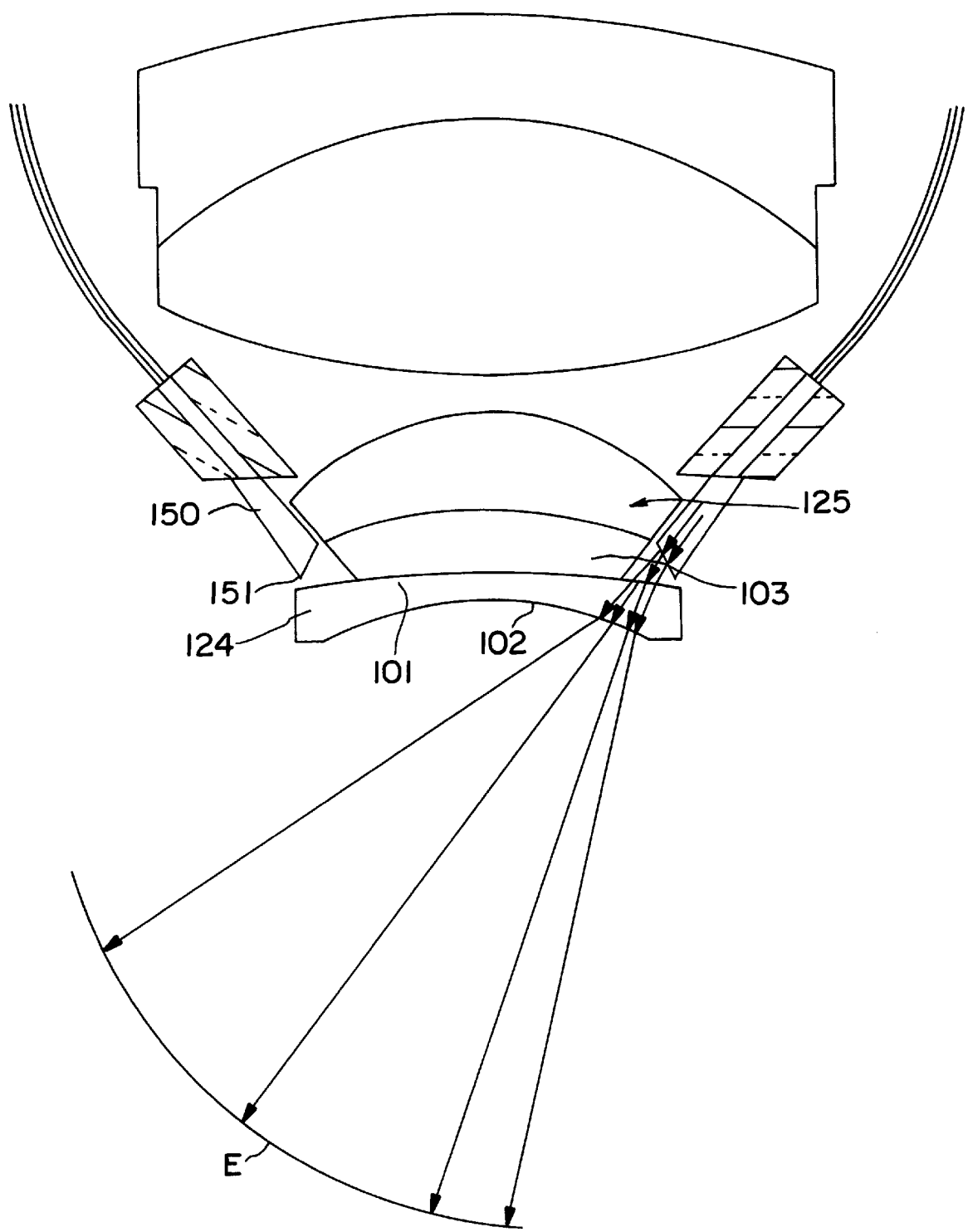
FIG. 6 is a side cross-sectional view of another embodiment of an optical system having improved central illumination.

Referring now to the embodiment of FIG. 6, the cornea contact glass lens 124 is provided with a power to provide assistance in directing the light from the end 151 of the light guide 150 towards the center of the eye E. For example, the lens 124 may be a plano-concave lens with a more planar back 101 and a concave front 102. Also the second part 103 of the front lens 125 can be made of the same glass as the lens 124 and since it contacts the back surface 101 of the lens 124 the power of the back surface 101 of the lens 124 does not matter in the optical system.

Figure 7:
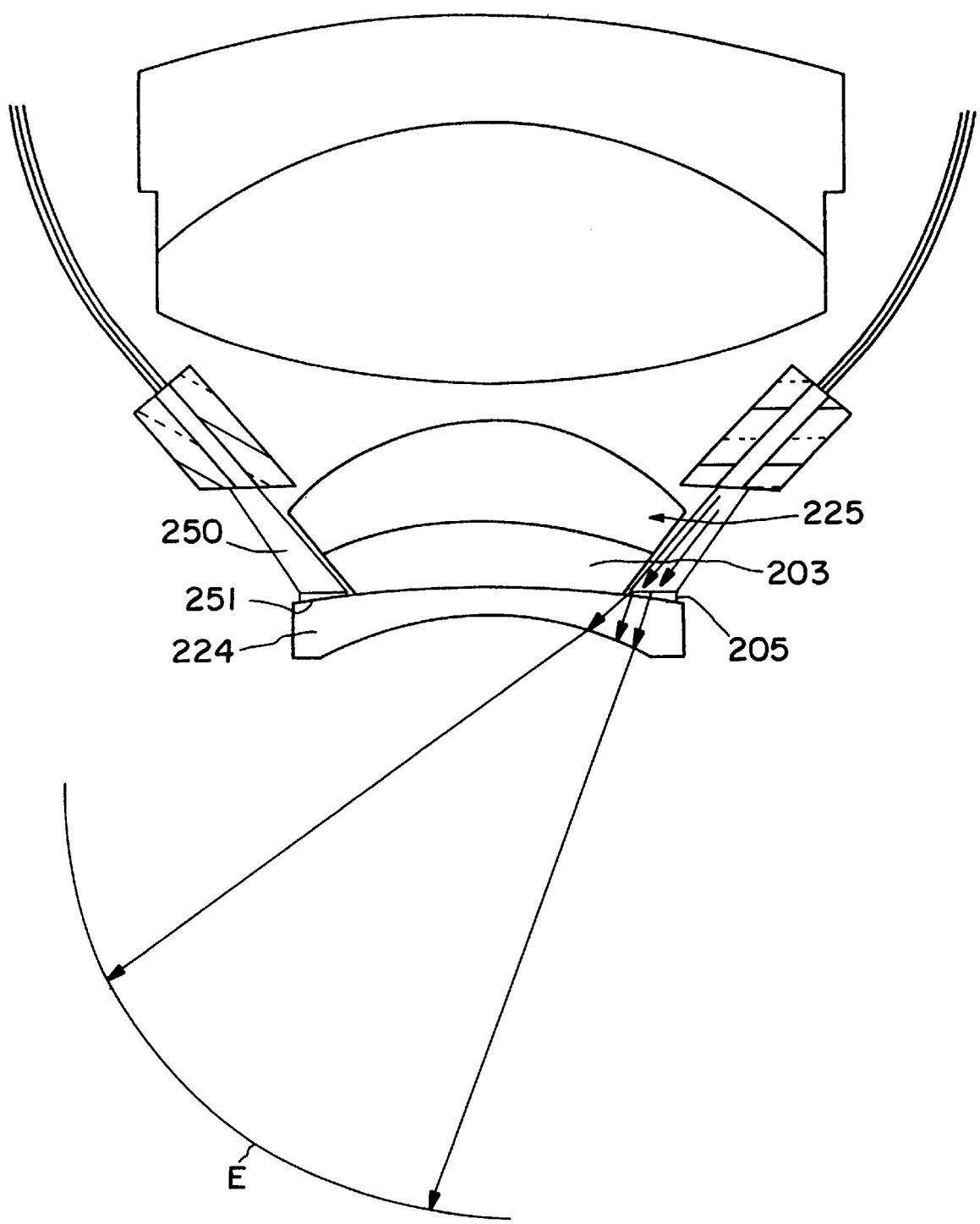
FIG. 7 is a side cross-sectional view of still another embodiment of an optical system having a still greater central illumination.
Figure 8:
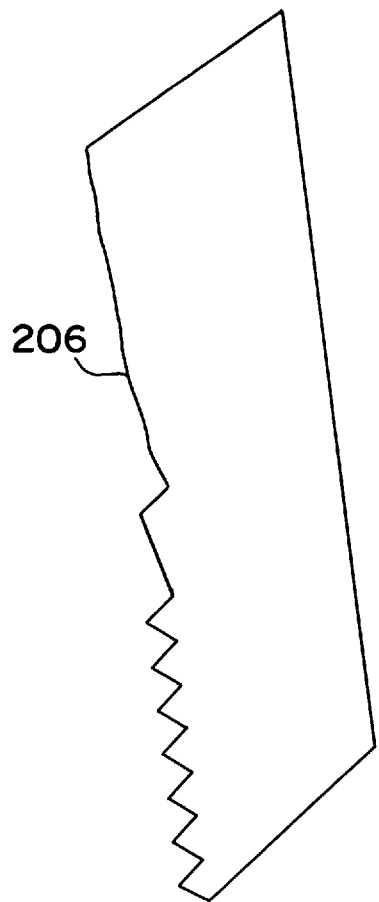
FIG. 8 is an enlarged cross-sectional view of the Fresnel lens used in the embodiment of FIG. 7.

A still more preferred embodiment is shown in FIGS. 7 and 8. Even with the embodiment of FIG. 6 the exit point from the end 151 of the light guide 150 is still moved outward from the center of the optical system by the required slope on the lens 103. This is a disadvantage since this requires yet a larger pupil on the human eye being measured. In the embodiment of FIG. 7, an additional lens 205 is positioned between the light guide 250 and the cornea contact lens 224 for additionally directing the light towards the center of the eye E. A Fresnel lens 206 (FIG. 8) has been found satisfactory. In addition, the end 251 of the light guide 250 is extended downwardly into contact with the additional lens 205. For example, the lens 205 could be placed on the end 251 of the light guide 250. This embodiment moves the source point for the light as far inward as is physically possible and is a relatively inexpensive design to fabricate.

The present invention provides a wide field image capture unit (ICU) using the light guide of FIGS. 3, 5A, 6 and 7 to obtain high quality color images with a very wide FOV typically at 120° to 150 degrees. It is light weight and can be hand-held. However, it could be mounted on a slit-lamp like apparatus as well, perhaps an ideal approach for cooperative adult patients. The ICU of the present invention further allows for easy insertion and removal of various light filters for angiography and/or different lenses or lens sets for varying FOV. Further, it is configured so that a lens set can be provided for imaging the front of the eye.

Figure 9:
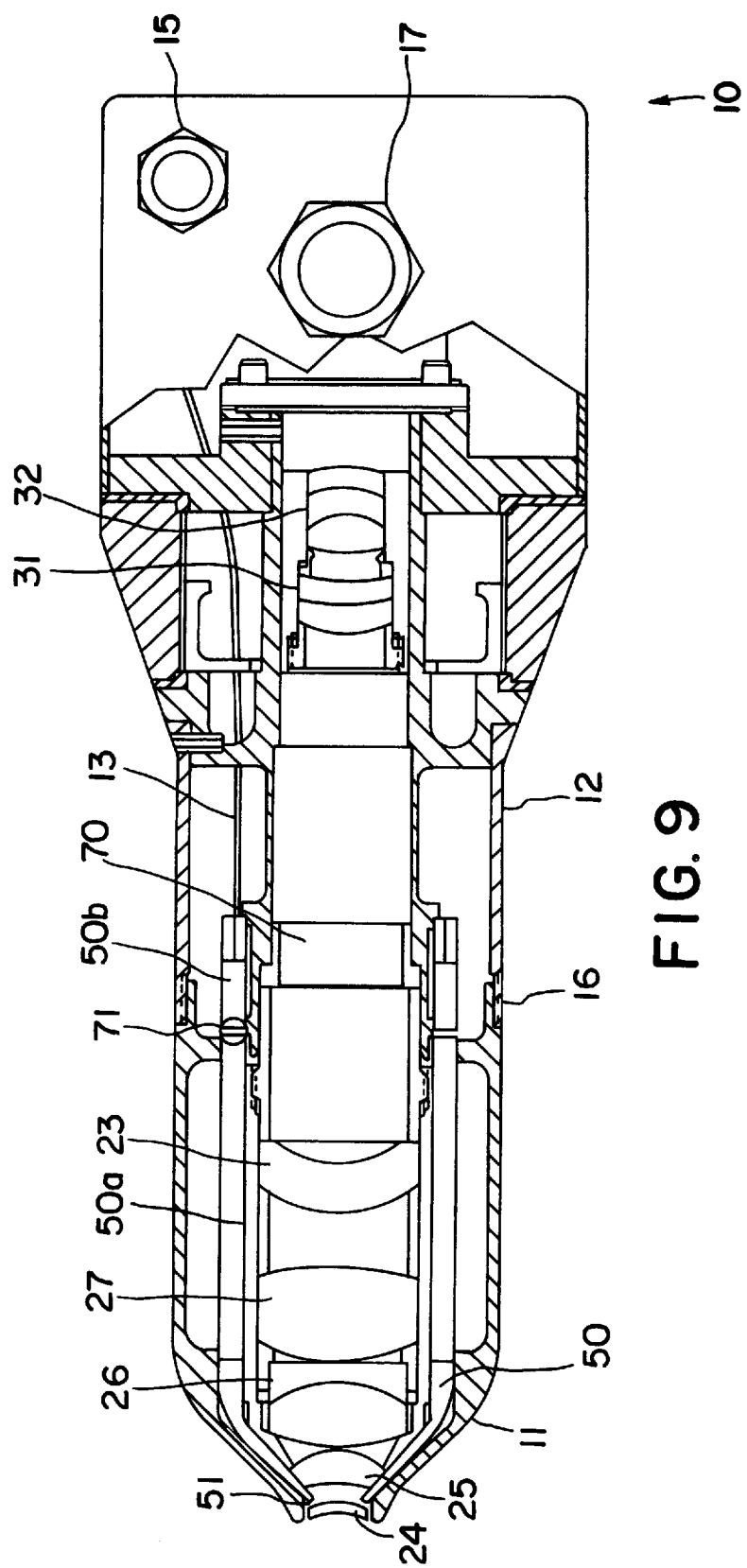
FIG. 9 is a detailed side cross-sectional view of the image capture unit (ICU) of the present invention.

A preferred embodiment of the ICU of the present invention is shown in FIG. 9. The reference numeral 10 indicates generally the image capture unit (ICU) of the present invention.

The ICU has a front housing 11 and a rear housing 12 which separate at the junction 16 which in general may be for example a locking thread. Located in the rear housing 12 are connectors for fiber optics power delivery 17 and for camera and control functions 15, all of which is shown in patent application Ser. No. 08/340,976 filed Nov. 17, 1994, entitled Eye Imaging System which is incorporated hereby by reference. The portable ICU may be held in the hand to be touched to the cornea. Focusing is accomplished thorough an internal mechanism which varies the distance between the front and rear lens sets. Alternatively, a light source may be mounted in the ICU eliminating the requirement for the external light delivery fiber optics cable.

Figure 10:
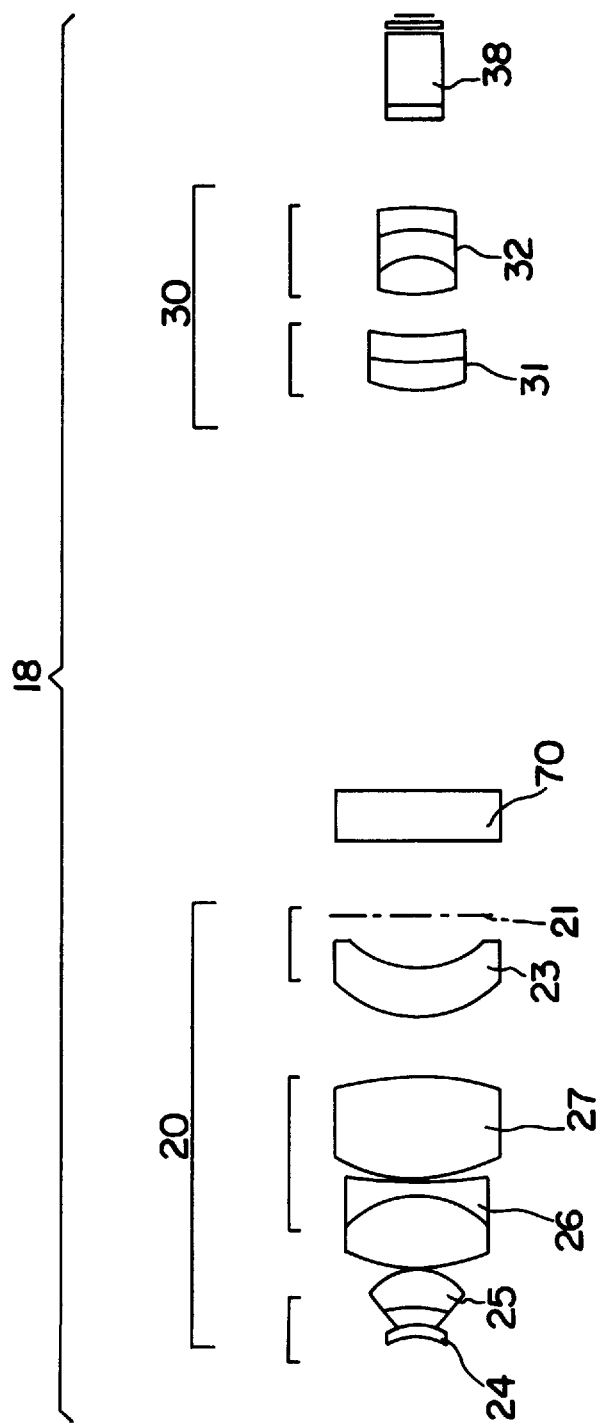
FIG. 10 is a cross-section view of the optical system.
Figure 11:
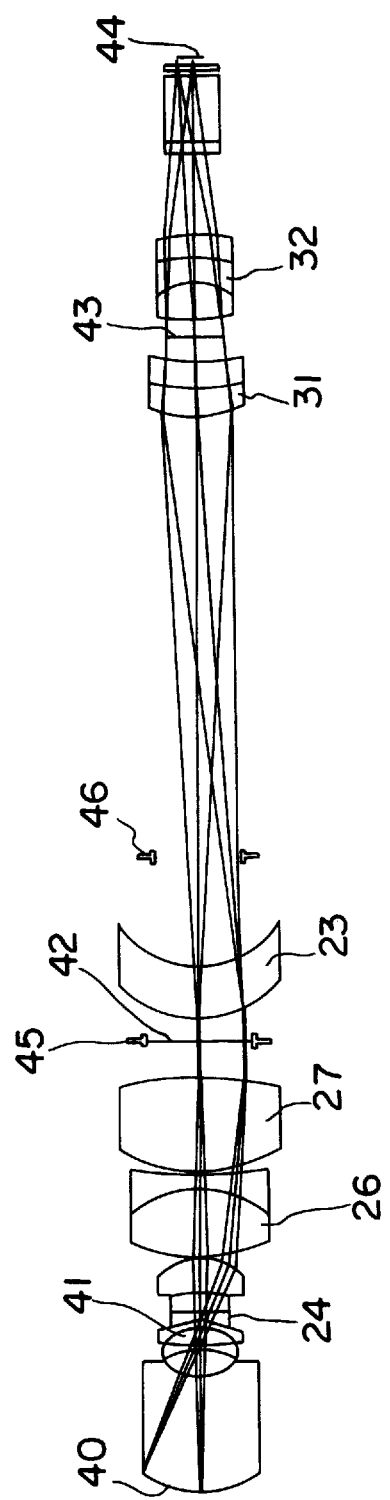
FIG. 11 is a cross-sectional view of the optical system showing key rays and locations of the pupils, objects, and images.
Figure 12:
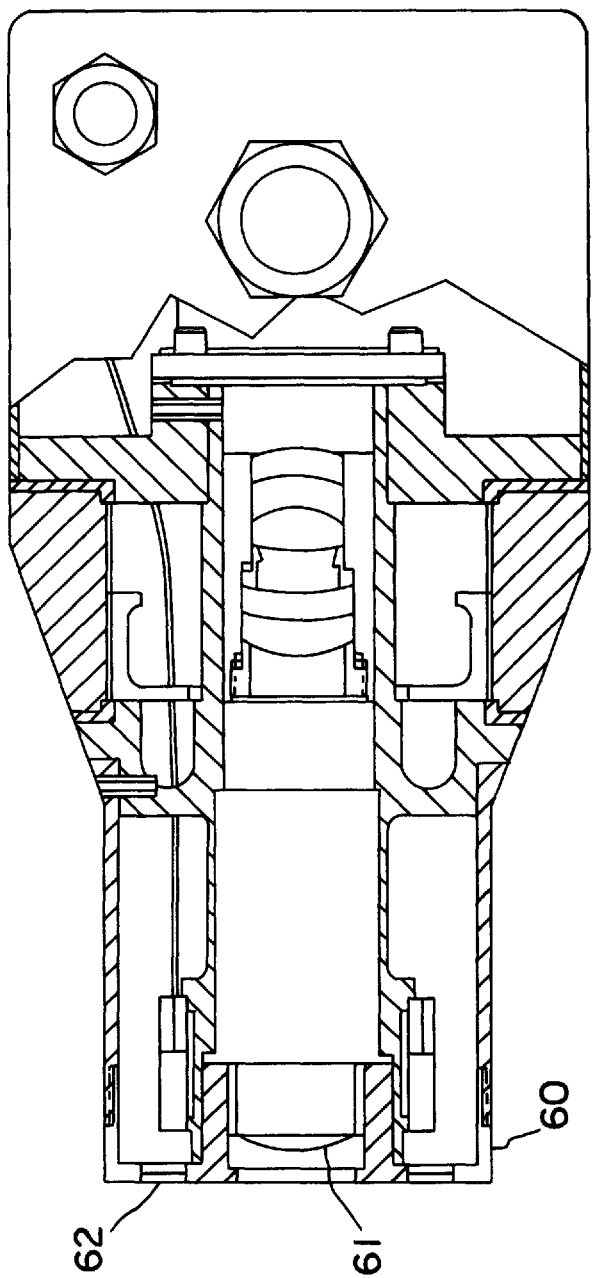
FIG. 12 is a cross-sectional view of the imaging and illuminating system for the front of the eye.

The lens systems, generally indicated by the reference numeral 18, as best seen in FIGS. 10 and 11, are divided into a front and rear set to accommodate focusing and pupil relaying functions. The front lens set 20 is comprised of a front doublet 25 with a wider contact or cornea lens 24 bonded onto the front and delivered to the system as a triplet. The next lens is a doublet 26 and then a singlet 27 followed by a meniscus 23 which may alternatively be an asphere to complete the front lens let. The rear lens set 30 is a doublet 31 and a triplet 32 for color aberration preventing means. And a chromatic charged coupled device 38 is positioned to receive the retina image.

The retina 40 is the object for the optical system and is re-imaged at image location 42 and then at the camera at image plane location 44. The system pupil is set by a mask at location 43 but is relayed to the eye lens at entrance pupil location 41.

The light guide 50 surrounds the corneal contact lens 24 so as to illuminate the eye through the cornea and has a shaped tip 51. A field stop is set by a mask at location 45 to define 120 degree FOV and block stray light. A stray light stop is set by a mask at location 46 to further blocked light reflected from the front lens.

Connecting cables between the ICU and the other components of a complete eye imaging device (including hardware for recording equipment) includes a control line for supplying and receiving information between the ICU and the other components, and an electrical cable for supplying power to the ICU all as disclosed in patent application Ser. No. 08/340,976. In addition, should the light source not be contained in the ICU, a light fiber optic cable 13 for supplying light from a light source outside the capture unit is included in the control line.

In the present invention, a one-piece, solid ring is used as a light guide 50. However, for ease of assembly the guide 50 may consist of extensions 50a and 50b which abut each other for light transfer. The tip 51 is shaped to bend the light to desired direction. A light absorption layer is coated on the selected portion of surface to reduce the stray light. Using a transparent light guide made as a ring from a single piece of plastic or glass has great advantages. In the prior art, the angle from which the light is aimed from the fiber is controlled by the location of the fiber on the radius of the cornea and is the normal to the cornea at the location of the ring.

In one embodiment, light is fed to the ICU 10 through a light fiber optic cable 13, which is contained in a connecting cable (not shown). The light fiber optic cable brings light to the ICU from a light source located in another component of an entire imaging device outside the ICU. In another embodiment, a light source is completely contained within the ICU 10.

The present invention provides a split housing 11 and 12 for the ICU 10 to allow for changing the front lens set 20 to accommodate different sizes and contours of the eye. For example, a different corneal contact lens 24 would be appropriate for an infant, as opposed to the corneal lens used on an adult. Further, it is a particular feature of the present invention that the front and rear lens sets 20 and 30 may be changed or re-positioned quickly and easily to accommodate insertion of filters 70 for various fluorescent angiographies or to accommodate lenses which provide different fields-of-view. A simple contact 71 between the front and rear sections 11 and 12 of the ICU 10 is sufficient for illumination transfer. The split housing makes it possible to remove the front lens set 20 completely, using the rear lens set 30 alone to image the front of the eye.

A further advantage of providing a split housing 11 is if the front housing is removed and then a special housing 60, as best seen in FIG. 9, inserted in its place which is designed to image the front of the eye through lens 61. The light already provided to the rear housing can be directed to a diffuser 62 which can then provide the illumination for the corneal image. Thus, the retinal camera can do double duty as a corneal imager.

These advantages are provided in a system which is practical to build; a goal not commercially realized until the present invention.

The present invention, therefore, is well adapted to carry out the objects and attain the ends and advantages mentioned, as well as other ends and advantages inherent herein. While presently preferred embodiments of the invention have been given for the purpose of disclosure, numerous changes in the details of construction and arrangement of parts may be made without departing from the spirit of the invention and the scope of the appended claims.

What is claimed is:

1. In an eye imaging portable image capture unit having a housing, a light source providing light in the housing for transmittal to an eye, imaging and focusing optics in the housing having a corneal contact lens for receiving reflected light from the eye through the cornea, an array image sensor in the housing for receiving light from the eye through the imaging and focusing optics in the housing, the improvement comprising,
a circular light guide positioned in the housing and positioned behind the corneal contact lens, said light guide including a solid one piece ring with a front end and a back end, said front end positioned at an angle converging inwardly and positioned adjacent the corneal contact lens, and said back end positioned to receive light from the light source.

2. The apparatus of claim 1 including a second light source providing axial directed light through the corneal contact lens for illuminating the central part of a retina.

3. The apparatus of claim 2 including a pupil mask having a central obstruction for reducing light backscatter.

4. The apparatus of claim 1 wherein the front end of the circular light guide directs overlapping light near the center of the retina of an eye.

5. The apparatus of claim 1 wherein the front end of the circular light guide has a divergence angle of greater than 40 degrees.

6. The apparatus of claim 5 wherein the divergence angle of light transmitted by the light guide is at least 120 degrees.

7. The apparatus of claim 5 wherein the front end of the light guide is shaped to direct the light transmitted in an optimal direction.

8. The apparatus of claim 1 wherein the corneal contact lens includes an optical shape for assisting in directing light from the circular light guide towards the center of the eye.

9. The apparatus of claim 8 wherein the corneal contact lens is a plano-concave shape.

10. The apparatus of claim 8 wherein the contact lens is of glass and the imaging and focusing optics includes a glass lens having a surface contacting the contact lens.

11. The apparatus of claim 8 including an additional lens positioned between the circular light guide and the corneal contact lens for additionally directing the light towards the center of the eye.

12. The apparatus of claim 11 wherein the additional lens is a Fresnel lens.

13. The apparatus of claim 11 wherein the front end of the circular light guide is extended into contact with the additional lens.

14. The eye imaging portable image capture unit comprising,
a housing,
a light source providing light in the housing for transmittal to an eye,
imaging and focusing optics in the housing having a front lens set and a rear lens set and a corneal contact lens positioned adjacent the front lens set, said contact lens having a larger diameter than the front lens set,
a chromatic charged coupled device in the housing for receiving light from the eye through the imaging and focusing optics,
a circular light guide positioned in the housing around the front lens set and behind the corneal contact lens, said light guide including a solid one-piece ring with a front end and a back end, said front end positioned at an angle converging inwardly and positioned against the corneal contact lens, and said back end positioned to receive light from the light source.

15. The apparatus of claim 14 wherein the housing includes a front part and a rear part, said parts being releasably connected, and the light guide includes a circular front end of the light guide extension aligned with the light guide and contacting the light guide for transmitting light therebetween.

16. The apparatus of claim 15 wherein the guide is positioned in the front part and the extension is positioned in the rear part for providing light when the front part is removed.

* * * * *

UNITED STATES PATENT AND TRADEMARK OFFICE
CERTIFICATE OF CORRECTION

PATENT NO. : 5,822,036
DATED : October 13, 1998
INVENTOR(S) : Massie et al

It is certified that error appears in the above-identified patent and that said Letters Patent is hereby corrected as shown below:

Column 10, line 42, delete "front end of the:

Column 10, line 43, after "the" insert - - front end of the - -

Signed and Sealed this

Eighteenth Day of July, 2000

Attest:

Q. TODD DICKINSON

Attesting Officer

Director of Patents and Trademarks